(12) United States Patent
Barth et al.

(10) Patent No.: US 7,390,924 B2
(45) Date of Patent: Jun. 24, 2008

(54) TERPHENYL DERIVATIVES, PREPARATION THEREOF, COMPOSITIONS CONTAINING SAME

(75) Inventors: Francis Barth, Saint Georges d'Orques (FR); Serge Martinez, Montpellier (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 244 days.

(21) Appl. No.: 10/511,040

(22) PCT Filed: Apr. 10, 2003

(86) PCT No.: PCT/FR03/01134

§ 371 (c)(1),
(2), (4) Date: Jul. 11, 2005

(87) PCT Pub. No.: WO03/084943

PCT Pub. Date: Oct. 16, 2003

(65) Prior Publication Data

US 2006/0167049 A1    Jul. 27, 2006

(30) Foreign Application Priority Data

Apr. 11, 2002    (FR) .................................. 02 04567

(51) Int. Cl.
C07C 233/00    (2006.01)
C07C 235/00    (2006.01)
C07C 237/00    (2006.01)
C07C 239/00    (2006.01)

(52) U.S. Cl. ..................................................... 564/161
(58) Field of Classification Search ................... 564/161
See application file for complete search history.

(56) References Cited

U.S. PATENT DOCUMENTS 4,916,145 A    4/1990  Tilley et al.

FOREIGN PATENT DOCUMENTS

FR    2800375    5/2001

OTHER PUBLICATIONS

Bass et al., SR-141716A-induced stimulation of locomotor activity. A structure-activity relationship study. Pharmacology, Biochemistry & Behavior, 74 (2002) 31-40.*

Brenna, B., et. al., New Route to O-Terphenyls: Application to the Synthesis of 6,7,10,11-Tetramethoxy-2-(Methoxycarbonyl)Triphenylene, J. Chem. Soc. Perkins Trans. 1, (1998) pp. 901-904.

Rinaldi-Carmona, M., et. al., SR141716A, A Potent and Selective Antogonist of the Brain Cannabinoid Receptor, Febs Letters, Elsevier Science Publishers, Amsterdam, NL, vol. 350, No. 2/3, (1994) pp. 240-244.

Sato, et. al., A New Route to Polycondensed Aromatics: Photolytic Formation of Triphenylene and Dibenzo[f,g, op]Naphthacene Ring Systems, Bulletin of The Chemical Society of Japan, vol. 44, pp. 2484-2490 (1971).

* cited by examiner

Primary Examiner—Yvonne Eyler
Assistant Examiner—Jennifer Y Cho
(74) Attorney, Agent, or Firm—Balaram Gupta

(57) ABSTRACT

The invention relates to terphenyl derivatives of formula:

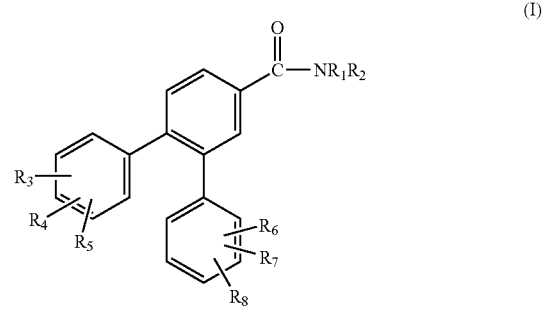

(I)

and to their preparation and to the pharmaceutical compositions comprising them.

These compounds exhibit an antagonist activity with respect to $CB_1$ cannabinoid receptors.

9 Claims, No Drawings

TERPHENYL DERIVATIVES, PREPARATION THEREOF, COMPOSITIONS CONTAINING SAME

CROSS REFERENCE TO RELATED APPLICATIONS

This application is a National Stage of International application No. PCT/FR03/01,134, filed Apr. 10, 2003, which is incorporated herein by reference in its entirety; which claims the benefit of priority of French Patent Application No. 02/04,567, filed Apr. 11, 2002.

The present invention relates to terphenyl derivatives, to their preparation and to pharmaceutical compositions comprising them.

Accordingly the present invention provides compounds of formula:

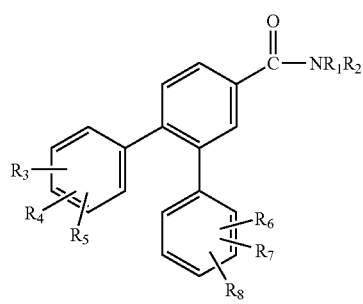

(I)

in which:
- $R_1$ represents hydrogen or a $(C_1-C_4)$alkyl;
- $R_2$ represents: a $(C_3-C_7)$ alkyl group,
  - an indan-1-yl or 1,2,3,4-tetrahydronaphthalen-1-yl group, said groups being unsubstituted or substituted by a halogen atom and/or a methyl group;
  - a saturated, single-nitrogen heterocyclic radical of 5 to 7 atoms, the nitrogen atom being substituted by a $(C_1-C_4)$alkyl, benzyl, $(C_1-C_3)$alkoxycarbonyl or $(C_1-C_4)$ alkanoyl group;
  - a group $NR_9R_{10}$;
  - a group $(CH_2)_nR_{11}$, $CH(CH_3)R_{11}$, $(CH_2)_mN(CH_3)R_{11}$;
  - a $C_3-C_{12}$ nonaromatic carbocyclic radical, unsubstituted or substituted one or more times by a methyl group;
- or $R_1$ and $R_2$ together with the nitrogen atom to which they are attached form either a piperazin-1-yl radical substituted in position 4 by a phenyl or benzyl group, or a piperidin-1-yl radical disubstituted in position 4 by a phenyl or benzyl group and by a $(C_1-C_4)$alkyl or $(C_1-C_3)$alkanoyl group; the phenyl or benzyl group substituents on the piperazin-1-yl radical or the piperidin-1-yl radical being unsubstituted or substituted by a halogen atom and/or a methyl group;
- $R_3$, $R_4$, $R_5$, $R_6$, $R_7$ and $R_8$ represent each independently of one another a hydrogen or halogen atom or a $(C_1-C_6)$ alkyl, $(C_1-C_6)$alkoxy or trifluoromethyl group;
- $R_9$ and $R_{10}$ together with the nitrogen atom to which they are attached form a saturated or unsaturated heterocyclic radical of 5 to 10 atoms containing or not containing a second heteroatom selected from O and N, said radical being unsubstituted or substituted one or more times by a $(C_1-C_4)$alkyl, hydroxyl or $(C_1-C_4)$alkoxy group;
- $R_{11}$ represents: a phenyl which is unsubstituted or substituted by one or more substituents selected from a halogen atom and a methyl group;
  - a heteroaryl radical of 6 to 10 atoms containing one or more nitrogen atoms;
- n represents 1, 2 or 3;
- m represents 0, 2 or 3;

and their salts, their solvates and their hydrates.

The compounds of formula (I) may exist in the form of bases or of addition salts with acids. These salts are advantageously prepared with pharmaceutically acceptable acids, although the salts of other acids useful, for example, for purifying or isolating compounds of formula (I) also form part of the invention.

An alkyl group is a linear or branched radical such as, in particular: methyl, ethyl, propyl, isopropyl, butyl, isobutyl, tert-butyl, n-pentyl, isopentyl, n-hexyl or isohexyl, the methyl group being preferred for a $(C_1-C_4)$alkyl and the tert-butyl, 2-methylbut-2-yl and 3,3-dimethylbut-2-yl groups being preferred for a $(C_1-C_6)$alkyl.

A $(C_1-C_6)$alkoxy group is a linear or branched radical containing 1 to 6 carbon atoms, the methoxy group being preferred.

A halogen atom is a fluorine, chlorine, bromine or iodine atom, fluorine, chlorine or bromine atoms being preferred.

The $C_3-C_{12}$ nonaromatic carbocyclic radicals comprise monocyclic or polycyclic, fused or bridged radicals. The monocyclic radicals include cycloalkyls, for example, cyclopropyl, cyclobutyl, cyclopentyl, cyclohexyl, cycloheptyl or cyclooctyl, cyclohexyl and cyclopentyl being preferred. The fused dicyclic or tricyclic radicals, bridged or in spiran form, include for example the radicals norbornyl, bornyl, isobornyl, noradamantyl, adamantyl, spiro[5.5]undecanyl and bicyclo [2.2.1]heptanyl, with spiro[5.5]undecanyl and bicyclo[2.2.1] heptanyl being preferred.

A saturated or unsaturated heterocyclic radical of 5 to 10 atoms, containing or not containing a second heteroatom such as O or N, embraces radicals such as morpholin-4-yl, piperidin-1-yl, piperazin-1-yl, pyrrolidin-1-yl, 3,6-dihydropyridin-1-yl and octahydrocyclopenta[c]pyrrol-2-yl, preference being given to the radicals pyrrolidin-1-yl, piperidin-1-yl and morpholin-4-yl.

Among the compounds according to the invention preference is given to the compounds of formula (I) in which:
- $R_1$ represents a hydrogen atom or a $(C_1-C_4)$alkyl group;
- $R_2$ represents a group $NR_9R_{10}$ or a nonaromatic $C_3-C_{12}$ carbocyclic radical which is unsubstituted or substituted one or more times by a methyl group;
- $R_3$, $R_4$, $R_5$, $R_6$, $R_7$ and $R_8$ represent each independently of one another a hydrogen or halogen atom or a $(C_1-C_6)$ alkyl, $(C_1-C_6)$alkoxy or trifluoromethyl group;
- $R_9$ and $R_{10}$ together with the nitrogen atom to which they are attached form a saturated or unsaturated heterocyclic radical of 5 to 10 atoms, containing or not containing a second heteroatom selected from O and N, said radical being unsubstituted or substituted one or more times by a $(C_1-C_6)$alkyl group;

and their salts, their solvates and their hydrates.

Among the compounds provided by the invention mention may be made of the preferred compounds which are defined by the following values for the substituents:
- $R_1$ represents a hydrogen atom; and/or
- $R_2$ represents a group selected from piperidin-1-yl, pyrrolidin-1-yl, cyclohexyl, spiro[5.5]undecanyl and 1,3,3-trimethylbicyclo[2.2.1]heptan-2-yl; and/or at least one of the substituents $R_3$, $R_4$ and $R_5$ represents a halogen atom or a trifluoromethyl group; and/or at least one of the substituents $R_6$, $R_7$ and $R_8$ represents a halogen atom.

The present invention further provides a process for preparing compounds of formula (I). This process is characterized in that a functional derivative of terphenylic acid of formula:

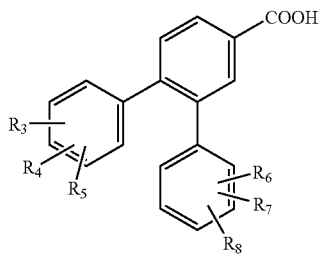
(II)

in which $R_3$, $R_4$, $R_5$, $R_6$, $R_7$ and $R_8$ are as defined for (I) is treated with an amine of formula $HNR_1R_2$ (III) in which $R_1$ and $R_2$ are as defined for (I). Optionally the compound thus obtained is converted into one of its salts and/or solvates.

As a functional derivative of the acid (II) it is possible to use the acid chloride, the anhydride, a mixed anhydride, a $C_1$-$C_4$ alkyl ester in which the alkyl is linear or branched, an activated ester, for example, the p-nitrophenyl ester or the appropriately activated free acid, activated for example with N,N-dicyclohexylcarbodiimide or with benzotriazol-1-yloxytris(dimethylamino)phosphonium hexafluorophosphate (BOP).

Thus in the process according to the invention the chloride of pyrazol-3-carboxylic acid, obtained by reacting thionyl chloride with the acid of formula (II), can be reacted with an amine $HNR_1R_2$ in an inert solvent such as a chlorinated solvent (dichloromethane, dichloroethane, or chloroform, for example), an ether (tetrahydrofuran or dioxane, for example) or an amide (N,N-dimethylformamide, for example) under an inert atmosphere at a temperature of between 0° C. and the ambient temperature in the presence of a tertiary amine such as triethylamine, N-methylmorpholine or pyridine.

One variant consists in preparing the mixed anhydride of the acid of formula (II) by reacting ethyl chloroformate with the acid of formula (II) in the presence of a base such as triethylamine and in reacting said mixed anhydride with an amine $HNR_1R_2$ in a solvent such as dichloromethane under an inert atmosphere at ambient temperature in the presence of a base such as triethylamine.

The acids of formula (II) can be prepared in accordance with the following scheme:

SCHEME 1

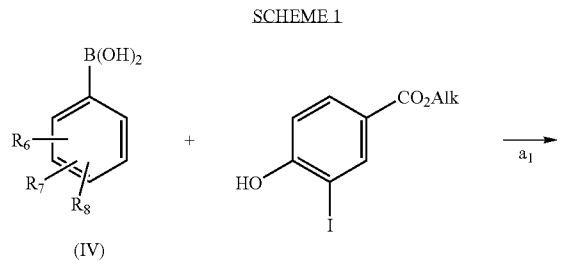

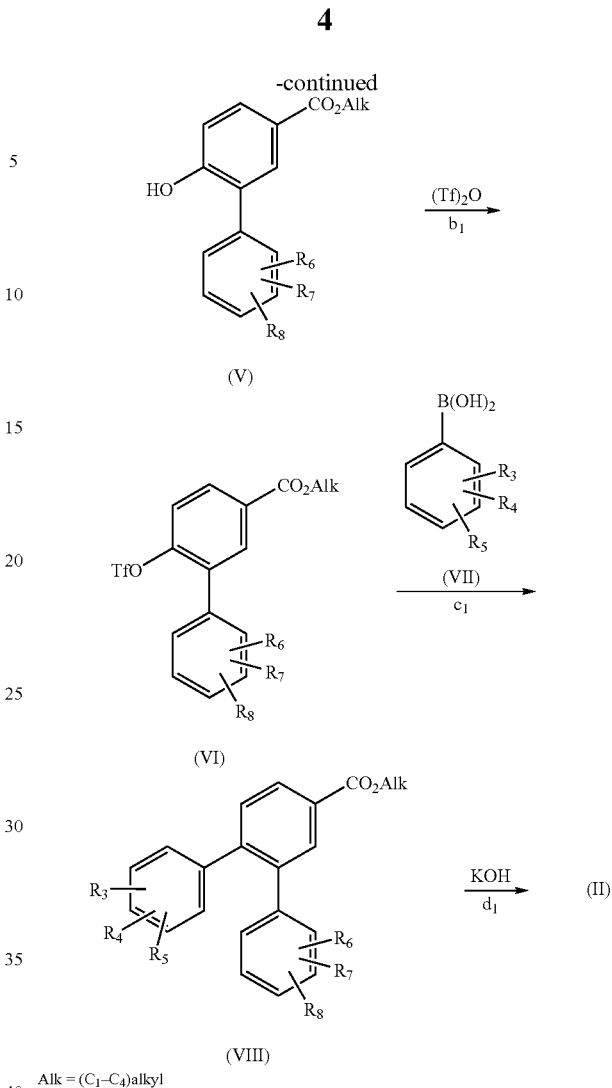

Alk = ($C_1$–$C_4$)alkyl

In step $a_1$ the reaction of the organoborate of formula (IV) with an ester of 4-hydroxy-3-iodobenzoic acid is carried out by the method of Farmaco Ed. Sci., 1958, 13, 121, using the conditions described by Suzuki in Helv. Chem. Acta, 1992, 75, 855.

In step $b_1$, the product is reacted with triflic anhydride (($Tf)_2O$) in pyridine in order to prepare the compound of formula (VI). That compound is coupled in step $c_1$ with an organoborate of formula (VII) under the conditions described in J. Org. Chem., 1992, 57, 379.

The terphenyl ester thus formed is subsequently hydrolyzed by known methods, in the presence of potassium hydroxide, for example, to give the acid of formula (II).

Compounds of formula (II) in which all of the substituents $R_3$ to $R_8$ are hydrogen are described in patent U.S. Pat. No. 4,916,145 and in the publication by T. Sato et al., Bull. Chem. Soc. Jap., 1971, 44(9), 2484-2490; the compounds of formula (II) in which the substituents $R_3$ and $R_6$ are simultaneously a 3-methoxy, a 4-methoxy or a 3-fluoro, the other substituents $R_4$, $R_5$, $R_6$, $R_7$ and $R_8$ being hydrogen, are described in patent U.S. Pat. No. 4,916,145; the compounds of formula (II) in which the substituents $R_3$, $R_4$ and $R_6$, $R_7$ are simultaneously 3,4-dimethoxy and the substituents $R_5$ and $R_8$ are hydrogen are described in the publication by E. Brenna, J. Chem. Soc. Perkin Trans. I, 1998, 901-904.

The other acids of formula (II) and their esters of formula (VIII) are new and constitute a final aspect of the invention. Accordingly, the present invention also provides compounds of formula:

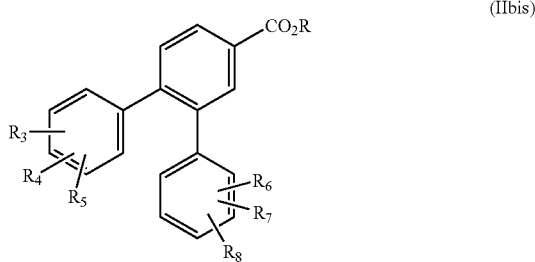

(IIbis)

in which $R_3$, $R_4$, $R_5$, $R_6$, $R_7$ and $R_8$ are as defined for (I) and R represents a hydrogen atom or a ($C_1$-$C_4$)alkyl group, on condition that $R_3$, $R_4$, $R_5$, $R_6$, $R_7$ and $R_8$ are not simultaneously hydrogen, and on condition that, when $R_4$, $R_5$, $R_7$ and $R_8$ represent hydrogen, $R_3$ and $R_6$ do not simultaneously represent a fluorine atom in meta position, or a methoxy group in meta or para position, and on condition that when $R_5$ and $R_8$ represent hydrogen $R_3$, $R_4$ and $R_5$, $R_6$ do not simultaneously represent 3,4-dimethoxy groups.

More particularly preference is given to the compounds of formula (IIa) in which:
- $R_3$ is in position 4 and represents a halogen atom or a trifluoromethyl group;
- $R_6$ is in position 2 and represents a hydrogen or halogen atom;
- $R_7$ is in position 4 and represents a halogen atom;
- $R_4$, $R_5$ and $R_8$ are hydrogen.

The amines $HNR_1R_2$ (III) are known or are prepared by known methods; by way of example mention may be made of: Chem. Ber. 1986, 119, 1413-1423.

The compounds of the formula (I) possess very good in vitro affinity ($IC_{50} \leq 10^{-7}$ M) for cannabinoid receptors $CB_1$, under the experimental conditions described by M. Rinaldi-Carmona et al. (FEBS Letters, 1994, 350, 240-244).

The antagonist nature of the compounds of formula (I) is demonstrated by the results obtained in adenylate cyclase inhibition models as described in M. Rinaldi-Carmona et al., J. Pharmacol. Exp. Ther., 1996, 278, 871-878.

The toxicity of the compounds of formula (I) is compatible with their use as a medicinal product.

In accordance with another of its aspects the present invention provides for the use of a compound of formula (I), or of one of its pharmaceutically acceptable salts, solvates or hydrates, for preparing medicinal products intended for treating diseases involving $CB_1$ cannabinoid receptors.

For example and without limitation, the compounds of formula (I) are useful as psychotropic medicinal products, particularly for treating psychiatric disorders, including anxiety, depression, mood disorders, insomnia, disorders involving delirium, obsessive disorders, psychoses in general, schizophrenia, and also for treating disorders linked to the use of psychotropic substances, particularly in the case of substance abuse and/or substance addiction, including alcohol addiction and nicotine addiction.

The compounds of formula (I) according to the invention can be used as medicinal products for treating migraine, stress, diseases of psychosomatic origin, panic attacks, epilepsy, locomotor disorders, especially dyskinesias or Parkinson's disease, shaking and dystonia.

The compounds of formula (I) according to the invention can also be used as medicinal products in treating memory disorders, cognitive disorders, especially in treating senile dementia and Alzheimer's disease, and also in the treatment of attention disorders or vigilance disorders. In addition the compounds of formula (I) may be useful as neuroprotective agents, in treating ischemia and cranial traumas and in treating neurodegenerative diseases, including chorea, Huntingdon's chorea and Tourette's syndrome.

The compounds of formula (I) according to the invention may be used as medicinal products in treating pain: neuropathic pain, peripheral acute pain, and chronic pain of inflammatory origin.

The compounds of formula (I) according to the invention may be used as medicinal products in treating appetite disorders, cravings (for sugars, carbohydrates, drugs, alcohols or any appetizing substance) and/or eating disorders, especially as anorexigenic agents or for treating obesity or bulimia, and also for treating type II diabetes or non-insulin-dependent diabetes. Moreover, the compounds of formula (I) according to the invention may be used as medicinal products in treating gastrointestinal disorders, diarrheic disorders, ulcers, vomiting, urinary and bladder disorders, disorders of endocrine origin, cardiovascular disorders, hypotension, hemorrhagic shock, septic shock, chronic cirrhosis of the liver, asthma, Raynaud's syndrome, glaucoma, fertility disorders, inflammatory phenomena, immune system diseases, especially autoimmune and neuroinflammatory diseases such as rheumatoid arthritis, reactional arthritis, diseases resulting in demyelinization, multiple sclerosis, infectious and viral diseases such as encephalitis, cerebrovascular accidents, and as medicinal products for anticancer chemotherapy and for treating Guillian-Barré syndrome.

According to the present invention the compounds of formula (I) are especially useful for treating psychotic disorders, especially schizophrenia; for treating appetite disorders and obesity; for treating memory and cognitive disorders; for treating alcohol addiction and nicotine addiction, in other words for alcohol withdrawal and tobacco withdrawal.

According to one of its aspects the present invention relates to the use of a compound of the formula (I), of its pharmaceutically acceptable salts and of their solvates or hydrates for treating the disorders and diseases indicated above.

The compound according to the invention is generally administered as a dosage unit.

Said dosage units are preferably formulated in pharmaceutical compositions in which the active principle is mixed with a pharmaceutical excipient.

Thus, according to another of its aspects, the present invention provides pharmaceutical compositions comprising as active principle a compound of formula (I), one of its pharmaceutically acceptable salts or one of their solvates.

The compound of formula (I) above and the pharmaceutically acceptable solvates or salts thereof can be used at daily doses of from 0.01 to 100 mg per kg of body weight of the mammal to be treated, preferably at daily doses of from 0.02 to 50 mg/kg. In humans the dose can vary preferably from 0.05 to 4000 mg per day, more particularly from 0.1 to 1000 mg per day, depending on the age of the individual to be treated or on the type of treatment, namely prophylactic or curative. Although these doses are examples of average situations, there may be particular cases where higher or lower doses are appropriate, and such doses also belong to the invention. In accordance with usual practice the dose which is appropriate for each patient is determined by the physician according to the method of administration and the age, weight and response of said patient.

In the pharmaceutical compositions of the present invention for oral, sublingual, inhaled, subcutaneous, intramuscular, intravenous, transdermal, local or rectal administration, the active principle can be administered in unit administration form, as a mixture with conventional pharmaceutical vehicles, to animals and to humans. The suitable unit administration forms comprise oral-route forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

In the pharmaceutical compositions of the present invention the active principle is generally formulated in dosage units containing from 0.05 to 1000 mg, advantageously from 0.1 to 500 mg, preferably from 1 to 200 mg of said active principle per dosage unit for daily administrations.

In the present description the following abbreviations are used:
DCM: dichloromethane
DMF: dimethylformamide
AcOEt: ethyl acetate
AT: ambient temperature
m.p.: melting point.

The compounds according to the invention are analyzed by LC/UV/MS coupling (liquid chromatography/UV detection/mass spectrometry). Measurements are made of the molecular peak ($M^+$) and the retention time (t) in minutes.

An Xterra Waters® MS C18 column is used, sold by Waters, measuring 2.1×30 mm, 3.5 µm, at ambient temperature, with a flow rate of 1 mL/minute.

The composition of the eluent is as follows:
solvent A: 0.025% trifluoroacetic acid (TFA) in water
solvent B: 0.025% TFA in acetonitrile.
Gradient: the percentage of solvent B varies from 0 to 100% in 2 minutes with a plateau at 100% of B for 1 minute.

UV detection is carried out between 210 nm and 400 nm and mass detection in chemical ionization mode at atmospheric pressure.

For interpreting the nuclear magnetic resonance (NMR) spectra the following abbreviations are used: s: singlet; d: doublet; m: unresolved multiplet; bs: broad singlet; dd: doublet of a doublet.

Preparation 1.1
(IIa): $R_3$, $R_4$, $R_5$=4-Cl; $R_6$, $R_7$, $R_8$=2,4-diCl. Methyl 4-2",4"-trichloro[1,1';2',1"]terphenyl-4'-carboxylate.

A) 4-Hydroxy-3-iodobenzoic Acid 30 g of 4-hydroxybenzoic acid are placed in 780 ml of water containing 18 g of sodium hydroxide, 49.5 g of sodium iodide are added, 675 ml of 3.5% sodium hypochlorite solution are run in slowly and the mixture is left with stirring at AT for 13 hours. 60 ml of concentrated $H_2SO_4$ are added and then, after cooling, the precipitate formed is filtered off and washed with water. This gives 32.46 g of the expected compound, m.p.=163° C.

B) Methyl 4-hydroxy-3-iodobenzoate 32.46 g of the acid obtained in the preceding step is placed in a mixture containing 138 ml of methanol and 10.36 ml of concentrated sulfuric acid and the mixture is heated at reflux for 3 and a half hours. The solvent is concentrated under vacuum and the residue is taken up in demineralized water and ethyl ether. It is neutralized with $Na_2CO_3$ and then the aqueous phase is extracted with AcOEt. The extract is washed with water and then with a saturated NaCl solution. This gives 32 g of the expected compound.

C) Methyl 2',4'-dichloro-6-hydroxy-(1,1'-biphenyl)-carboxylate 5.6 g of methyl 4-hydroxy-3-iodobenzoate are introduced under argon into 50 ml of anhydrous DMF and then 4.2 g of 2,4-dichlorophenylboronic acid and 5.54 ml of triethylamine and then 240 mg of tri-orthotolylphosphine are added and the mixture is left under argon for 1 hour. 180 mg of palladium acetate are added and then the mixture is heated at 100° C. for 4 hours. 2 g of 2,4-dichlorophenylboronic acid, 5.54 ml of triethylamine, 120 mg of tri-orthotolylphoshine and 180 mg of palladium acetate are added and then the mixture is heated at 100° C. for 8 hours. It is concentrated under vacuum and the residue is taken up in AcOEt and then washed with 10% $NH_4OH$ solution. Extraction is carried out with AcOEt and the extract is washed with water and then with saturated NaCl solution. The residue is dried and then chromatographed on silica, eluting with a cyclohexane/AcOEt mixture (82/18; v/v), to give 3.4 g of the expected compound.

D) Methyl 2',4'-dichloro-6-((trifluoromethyl-sulfonyl)oxy)(1,1'-biphenyl)-3-carboxylate 3.27 g of the compound obtained in the preceding step are placed in 150 ml of pyridine, the mixture is cooled to between 0° C. and 5° C. and 2.8 ml of triflic anhydride are run in dropwise. The mixture is maintained with stirring at AT overnight and then concentrated to dryness. The residue is chromatographed on silica, eluting with a cyclohexane/AcOEt mixture (90/10; v/v), to give 3.2 g of the expected compound.

E) Methyl 4,2",4"-trichloro[1,1';2',1"]terphenyl-4'-carboxylate 3.2 g of the compound obtained in the preceding step are placed in 75 ml of toluene and 2.33 g of 4-chlorophenylboronic acid are added and then 1.55 g of potassium carbonate. The mixture is left under argon for 30 minutes and then 1.38 g of tetrakis(triphenylphosphine)palladium are added and the reaction mixture is heated at between 80° C. and 85° C. for 3 hours. It is left overnight at AT and then diluted with AcOEt and washed with 5% $Na_2CO_3$ solution (twice) and then with saturated NaCl solution. It is dried and then the residue is chromatographed on silica with a cyclohexane/AcOEt mixture (80/20; v/v) to give 1.83 g of the expected compound, which crystallizes from isopropyl ether, m.p.=136° C.

The procedure described above is used to prepare the methyl esters of the acids of formula (II) collated in the table below.

TABLE 1

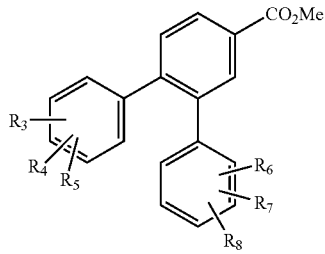

(IIa)

| Preparations | $R_3, R_4, R_5$ | $R_6, R_7, R_8$ | m.p. °C./NMR |
|---|---|---|---|
| 1.2 | 4-Cl | 4-Cl | 223° C. |
| 1.3 | 4-F | 2,4-diCl | NMR(DMSO-$d_6$) δ ppm: 6.9: m: 4H; 7.25: d: 1H; 7.35: dd: 1H; 7.55: m: 2H; 7.80: d: 1H; 8.00: dd: 1H; 13.20: bs: 1H |
| 1.4 | 4-$CF_3$ | 2,4-diCl | 206° C. |

EXAMPLE 1

Compound I 4,2",4"-Trichloro(N-1-piperidinyl)[1,1';2',1"]-terphenyl-4'carboxamide.

(I):

$R_1 = H$;  $R_2 = $ —N⟨piperidinyl⟩ ;  $R_3, R_4, R_5 = 4$-Cl;  $R_6, R_7,$ $R_8 = 2,4$-diCl

A) 4,2",4"-Trichloro[1,1,';2',1"]terphenyl-4'-carboxylic acid 1.33 g of the compound from Preparation 1.1 is suspended in 30 ml of ethanol, 0.95 g of potassium hydroxide in solution in 5 ml of water is added and the mixture is heated at reflux for 2 hours. After cooling to AT it is filtered over Célite® and concentrated to dryness under vacuum. The residue is taken up in 30 ml of water and then acidified to a pH of 1 by adding 1N HCl. The mixture is cooled using an ice bath and then extracted with AcOEt. It is washed with water and then with saturated NaCl solution to give 1.22 g of the expected compound, m.p.=237° C.

B) 4,2",4"-Trichloro[1,1';2',1"]terphenyl-4'-carboxylic chloride 500 mg of the acid obtained in the preceding step are suspended in 50 ml of toluene, 0.3 ml of thionyl chloride is added and the mixture is heated at reflux for 2 hours. The solvent is concentrated twice to give 0.52 g of the expected compound in solid form.

C) 4,2",4"-Trichloro(N-1-piperidinyl) [1,1';2',1"]-terphenyl-4'-carboxamide

A solution containing 0.17 ml of aminopiperidine and 0.22 ml of triethylamine in 10 ml of DCM is prepared, this solution is cooled to between 0° C. and 5° C. and 0.52 g of the acid chloride obtained in the preceding step in 10 ml of DCM is added dropwise. The mixture is left at +4° C. for 2 days. It is poured into ice-water, then extracted with DCM and washed with 5% $Na_2CO_3$ solution and then with saturated NaCl solution. The extracts are dried and then the residue is chromatographed on silica, eluting with a toluene/AcOEt mixture (88/12; v/v). This gives 0.3 g of the expected compound, m.p.=182° C.

The procedure of Example 1 is used to prepare the compounds of the invention which are described below.

TABLE 2

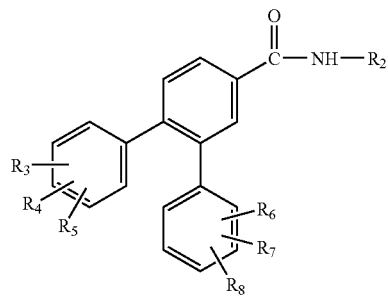

(I)

| Compounds | $R_1$ | $R_2$ | $R_3, R_4, R_5$ | $R_6, R_7, R_8$ | Characterization |
|---|---|---|---|---|---|
| 1 | H | —N⟨piperidinyl⟩ | 4-Cl | 2,4-diCl | m.p. = 182° C. |
| 2 | H | —N⟨piperidinyl⟩ | 4-Cl | 4-Cl | m.p. = 233° C. |

TABLE 2-continued
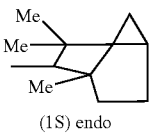
(I)
| Compounds | R₁ | R₂ | R₃, R₄, R₅ | R₆, R₇, R₈ | Characterization |
|---|---|---|---|---|---|
| 3 | H | 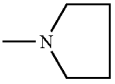 (1S) endo | 4-Cl | 2,4-diCl | m.p. = 98° C. |
| 4 | H | 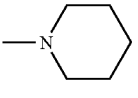 | 4-Cl | 2,4-diCl | m.p. = 168° C. |
| 5 | H | 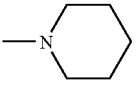 | 4-F | 2,4-diCl | m.p. = 175° C. |
| 6 | H | 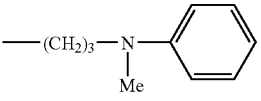 | 4-CF₃ | 2,4-diCl | m.p. = 177° C. |
| 7 | H | 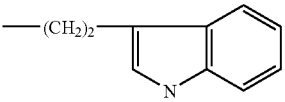 | 4-Cl | 4-Cl | M⁺ = 489.49<br>t = 1.95 |
| 8 | H | 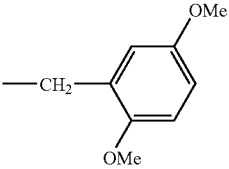 | 4-Cl | 4-Cl | M⁺ = 484.95<br>t = 2.33 |
| 9 | H | 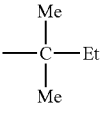 | 4-Cl | 4-Cl | M⁺ = 492.15<br>t = 2.28 |
| 10 | H | —C(Me)(Me)Et | 4-Cl | 4-Cl | M⁺ = 411.98<br>t = 2.43 |
| 11 | H | 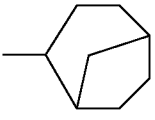 | 4-Cl | 4-Cl | M⁺ = 450.50<br>t = 2.43 |

TABLE 2-continued

| Compounds | $R_1$ | $R_2$ | $R_3, R_4, R_5$ | $R_6, R_7, R_8$ | Characterization |
|---|---|---|---|---|---|
| 12 | —$NR_1R_2$ | 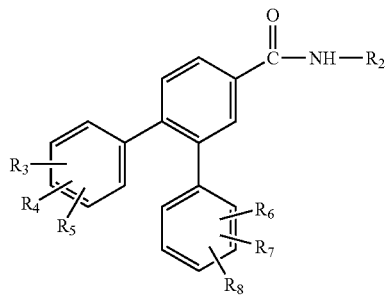 | 4-Cl | 4-Cl | $M^+ = 514.42$<br>t = 2.50 |

The invention claimed is:

1. A compound of formula (I):

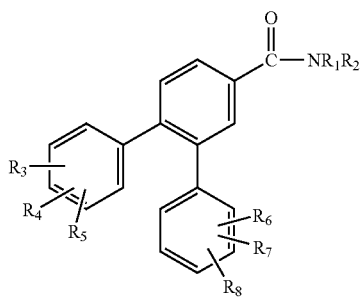

in which:

$R_1$ represents hydrogen or a $(C_1\text{-}C_4)$alkyl;

$R_2$ represents: a $(C_3\text{-}C_7)$alkyl group,
an indan-1-yl or 1,2,3,4-tetrahydronaphthalen-1-yl group, said groups being unsubstituted or substituted by a halogen atom or a methyl group;
a saturated, single-nitrogen heterocyclic radical of 5 to 7 atoms, the nitrogen atom being substituted by a $(C_1\text{-}C_4)$alkyl, benzyl, $(C_1\text{-}C_3)$alkoxycarbonyl or $(C_1\text{-}C_4)$alkanoyl group;
a group $NR_9R_{10}$;
a group $(CH_2)_nR_{11}$, $CH(CH_3)R_{11}$, $(CH_2)_mN(CH_3)R_{11}$;
a $C_3\text{-}C_{12}$ nonaromatic carbocyclic radical, unsubstituted or substituted one or more times by a methyl group;
or $R_1$ and $R_2$ together with the nitrogen atom to which they are attached form either a piperazin-1-yl radical substituted in position 4 by a phenyl or benzyl group, or a piperidin-1-yl radical disubstituted in position 4 by a phenyl or benzyl group and by a $(C_1\text{-}C_4)$alkyl or $(C_1\text{-}C_3)$alkanoyl group; the phenyl or benzyl group substituents on the piperazin-1-yl radical or the piperidin-1-yl radical being unsubstituted or substituted by a halogen atom or a methyl group;

$R_3, R_4, R_5, R_6, R_7$ and $R_8$ represent each independently of one another a hydrogen or halogen atom or a $(C_1\text{-}C_6)$alkyl, $(C_1\text{-}C_6)$alkoxy or trifluoromethyl group;

$R_9$ and $R_{10}$ together with the nitrogen atom to which they are attached form a saturated or unsaturated heterocyclic radical of 5 to 10 atoms containing or not containing a second heteroatom selected from O and N, said radical being unsubstituted or substituted one or more times by a $(C_1\text{-}C_4)$alkyl, hydroxyl or $(C_1\text{-}C_4)$alkoxy group;

$R_{11}$ represents: a phenyl which is unsubstituted or substituted by one or more substituents selected from a halogen atom and a methyl group;

n represents 1, 2 or 3; and m represents 0, 2 or 3; or a salt, thereof.

2. A compound according to claim 1 of formula (I) in which:

$R_1$ represents a hydrogen atom or a $(C_1\text{-}C_4)$alkyl group;

$R_2$ represents a group $NR_9R_{10}$ or a nonaromatic $C_3\text{-}C_{12}$ carbocyclic radical which is unsubstituted or substituted one or more times by a methyl group;

$R_3, R_4, R_5, R_6, R_7$ and $R_8$ represent each independently of one another a hydrogen or halogen atom or a $(C_1\text{-}C_6)$alkyl, $(C_1\text{-}C_6)$alkoxy or trifluoromethyl group; and $R_9$ and $R_{10}$ together with the nitrogen atom to which they are attached form a saturated or unsaturated heterocyclic radical of 5 to 10 atoms, containing or not containing a second heteroatom selected from O and N, said radical being unsubstituted or substituted one or more times by a $(C_1\text{-}C_4)$alkyl group; or a salt, thereof.

3. A compound according to claim 1 of formula (I) in which:

$R_1$ represents a hydrogen atom;

$R_2$ represents a group selected from piperidin-1-yl, pyrrolidin-1-yl, cyclohexyl, spiro[5.5]undecanyl and 1,3,3-trimethylbicyclo[2.2.1]heptan-2-yl;

at least one of the substituents $R_3$, $R_4$ and $R_5$ represents a halogen atom or a trifluoromethyl group; and at least one of the substituents $R_6$, $R_7$ and $R_8$ represents a halogen atom.

4. A process for preparing a compound of formula (I) according to claim 1 wherein a functional derivative of terphenylic acid of formula:

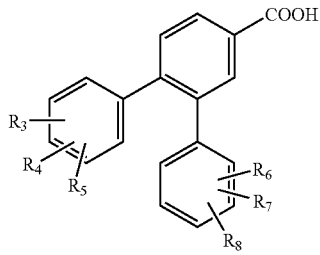

(II)

in which $R_3$, $R_4$, $R_5$, $R_6$, $R_7$ and $R_8$ are as defined for a compound of formula (I) in claim 1 is treated with an amine of formula $HNR_1R_2$ (III) in which $R_1$ and $R_2$ are as defined for a compound of formula (I) in claim 1.

5. A pharmaceutical composition which comprises a compound of formula (I) according to claim 1 or one of its pharmaceutically acceptable salts, hydrates or solvates, and at least one pharmaceutically acceptable excipient.

6. A compound according to claim 2 of formula (I) in which:

$R_1$ represents a hydrogen atom or a $(C_1\text{-}C_4)$alkyl group;

$R_2$ represents a group $NR_9R_{10}$ or a nonaromatic $C_3\text{-}C_{12}$ carbocyclic radical which is unsubstituted or substituted one or more times by a methyl group;

$R_3$, $R_4$, $R_5$, $R_6$, $R_7$ and $R_8$ represent each independently of one another a hydrogen or halogen atom or a $(C_1\text{-}C_6)$ alkyl, $(C_1\text{-}C_6)$alkoxy or trifluoromethyl group; and $R_9$ and $R_{10}$ together with the nitrogen atom to which they are attached form a saturated or unsaturated heterocyclic radical of 5 to 10 atoms, containing or not containing a second heteroatom selected from O and N, said radical being unsubstituted or substituted one or more times by a $(C_1\text{-}C_4)$alkyl group; or a salt, thereof.

7. A pharmaceutical composition which comprises a compound of formula (I) according to claim 2 or one of its pharmaceutically acceptable salts, hydrates or solvates, and at least one pharmaceutically acceptable excipient.

8. A pharmaceutical composition which comprises a compound of formula (I) according to claim 3 or one of its pharmaceutically acceptable salts, hydrates or solvates, and at least one pharmaceutically acceptable excipient.

9. A pharmaceutical composition which comprises a compound of formula (I) according to claim 6 or one of its pharmaceutically acceptable salts, hydrates or solvates, and at least one pharmaceutically acceptable excipient.

* * * * *